US007799940B2

(12) United States Patent
Vic Fernandez et al.

(10) Patent No.: US 7,799,940 B2
(45) Date of Patent: Sep. 21, 2010

(54) PROCESS FOR MANUFACTURING DIMETHYL CARBONATE

(75) Inventors: Ignacio Vic Fernandez, Madrid (ES); Benoit Fillion, Murcia (ES); Vutukuru Murthy, Bangalore (IN); Vinod Sankaran Nair, Bangalore (IN); Mario Perez Collado, Murcia (ES)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 219 days.

(21) Appl. No.: 12/032,149

(22) Filed: Feb. 15, 2008

(65) Prior Publication Data

US 2008/0200713 A1 Aug. 21, 2008

Related U.S. Application Data

(60) Provisional application No. 60/890,288, filed on Feb. 16, 2007.

(51) Int. Cl.
C07C 69/96 (2006.01)
(52) U.S. Cl. .................................................. 558/277
(58) Field of Classification Search .................. 558/277
See application file for complete search history.

(56) References Cited

U.S. PATENT DOCUMENTS

| 5,210,268 | A | 5/1993 | Fukuoka et al. |
| 5,380,908 | A | 1/1995 | Murata et al. |
| 5,426,207 | A | 6/1995 | Harrison et al. |
| 5,523,451 | A | 6/1996 | Rechner et al. |
| 5,527,943 | A | 6/1996 | Rivetti et al. |
| 5,536,864 | A | 7/1996 | Paret et al. |
| 5,599,965 | A | 2/1997 | Kricsfalussy et al. |
| 5,872,275 | A | 2/1999 | Komiya et al. |
| 6,093,842 | A | 7/2000 | Oyevaar et al. |
| 6,197,918 | B1 | 3/2001 | Uno et al. |
| 6,262,210 | B1 | 7/2001 | Tojo et al. |
| 6,315,868 | B1 | 11/2001 | Nisoli et al. |
| 6,392,078 | B1 | 5/2002 | Ryu et al. |
| 6,977,308 | B2 * | 12/2005 | van de Broek et al. ...... 558/277 |
| 7,622,602 | B2 * | 11/2009 | Ramgopal et al. ........... 558/277 |
| 2001/0021786 | A1 | 9/2001 | Bruin et al. |
| 2007/0191623 | A1 | 8/2007 | Fukuoka et al. |
| 2007/0197814 | A1 | 8/2007 | Van Der Heide et al. |
| 2007/0197815 | A1 | 8/2007 | Van Der Heide et al. |
| 2007/0197816 | A1 | 8/2007 | Van Der Heide et al. |
| 2007/0219387 | A1 | 9/2007 | Fukuoka et al. |
| 2007/0255069 | A1 | 11/2007 | Fukuoka et al. |
| 2007/0260083 | A1 | 11/2007 | Fukuoka et al. |
| 2007/0260084 | A1 | 11/2007 | Fukuoka et al. |
| 2007/0260095 | A1 | 11/2007 | Fukuoka et al. |
| 2007/0265461 | A1 | 11/2007 | Fukuoka et al. |
| 2007/0270604 | A1 | 11/2007 | Fukuoka et al. |

FOREIGN PATENT DOCUMENTS

| CN | 1210850 | 3/1999 |
| CN | 1212172 | 3/1999 |
| CN | 1271721 | 11/2000 |
| EP | 0000894 A1 | 3/1979 |
| EP | 0001780 A1 | 5/1979 |
| EP | 0781760 A1 | 7/1997 |
| EP | 1156028 A1 | 11/2001 |
| EP | 1762559 A1 | 3/2007 |
| EP | 1783112 A1 | 5/2007 |
| EP | 1787976 A1 | 5/2007 |
| EP | 1792890 A1 | 6/2007 |
| EP | 1795522 A1 | 6/2007 |
| EP | 1795523 A1 | 6/2007 |
| GB | 1470160 | 4/1977 |
| JP | 63205101 | 8/1988 |
| JP | 05221929 | 8/1993 |
| JP | 06145113 | 5/1994 |
| JP | 06145114 | 5/1994 |
| JP | 06184055 | 7/1994 |
| JP | 06228026 | 8/1994 |
| JP | 2000191594 | 7/2000 |
| JP | 2001064235 | 3/2001 |

OTHER PUBLICATIONS

Li, et al., "Study on extractive distillation of methanol and dimethyl carbonate azeotrope using furfural extractant", Department of Chemistry, Huazhong Univeristy of Science and Technology, (2000), pp. 12-13, vol. 28(4), Publisher: Huaxu Gongyebu Di-6 Shejiyuan.

Xiong et al., "Separation of binary methanol-dimethyl carbonate azeotrope", Journal: General Review written in Chinese (with English Abstract), (2002), pp. 26-28, vol. 21(1); Publisher: Huaxue Gongye Chubanshe, China.

Han et al., "Development in Separation of Dimethyl Carbonate-Methanol Azeotrope", Journal: Jiangsu Polytechnic University (with English Abstract), (2003), pp. 61-64, vol. 15, Part 4.

Wei et al., "Separation of dimethyl carbonate from methanol-dimethyl carbonate azeotrope", Taiyuan University of Technology, Taiyuan, Peoples Republic of China. Huagong Jinzhan, (2005), pp. 1234-1238, vol. 24(11).

* cited by examiner

*Primary Examiner*—Rei-tsang Shiao
(74) *Attorney, Agent, or Firm*—Larson & Anderson, LLC (57) ABSTRACT

The present invention provides methods of forming dialkyl carbonate wherein catalyst buildup in the reaction equipment, the separation equipment, and transfer lines there between is reduced and even eliminated. In one embodiment, the method includes introducing alkanol, carbon monoxide, oxygen, and a catalyst to a reactor having a gaseous head space and a liquid body space. The reactor is operated under conditions to form dialkyl carbonate and water. A product stream containing dialkyl carbonate, water, and residual reactants is removed from the head space of the reactor and introduced to a cyclone with a flushing stream. A liquid bottom stream is captured from the cyclone and introduced to the reactor. The gaseous top stream contains product dialkyl carbonate.

22 Claims, 9 Drawing Sheets

Figure 8

PROCESS FOR MANUFACTURING DIMETHYL CARBONATE

CROSS-REFERENCE TO RELATED APPLICATION

The present application claims priority from and is a nonprovisional application of US Provisional Patent Application Ser. No. 60/890,288 filed on Feb. 16, 2007, which is incorporated by reference for all purposes.

BACKGROUND OF THE INVENTION

Diaryl carbonates, such as diphenyl carbonate, are an important reactant in the production of polycarbonate resins. As the uses to which polycarbonates are put have increased, the safe and efficient production of diaryl carbonates has become of greater significance. Early processes for the production of diaryl carbonates utilized phosgene as a reagent. The toxicity of phosgene, however, prompted the development of a non-phosgene process. The non-phosgene process is well-known in the art and is described in U.S. Pat. Nos. 4,410,464, 5,344,954, 6,784,277, 7,141,641, and 7,288,668, which are incorporated herein by reference.

Figure 1:
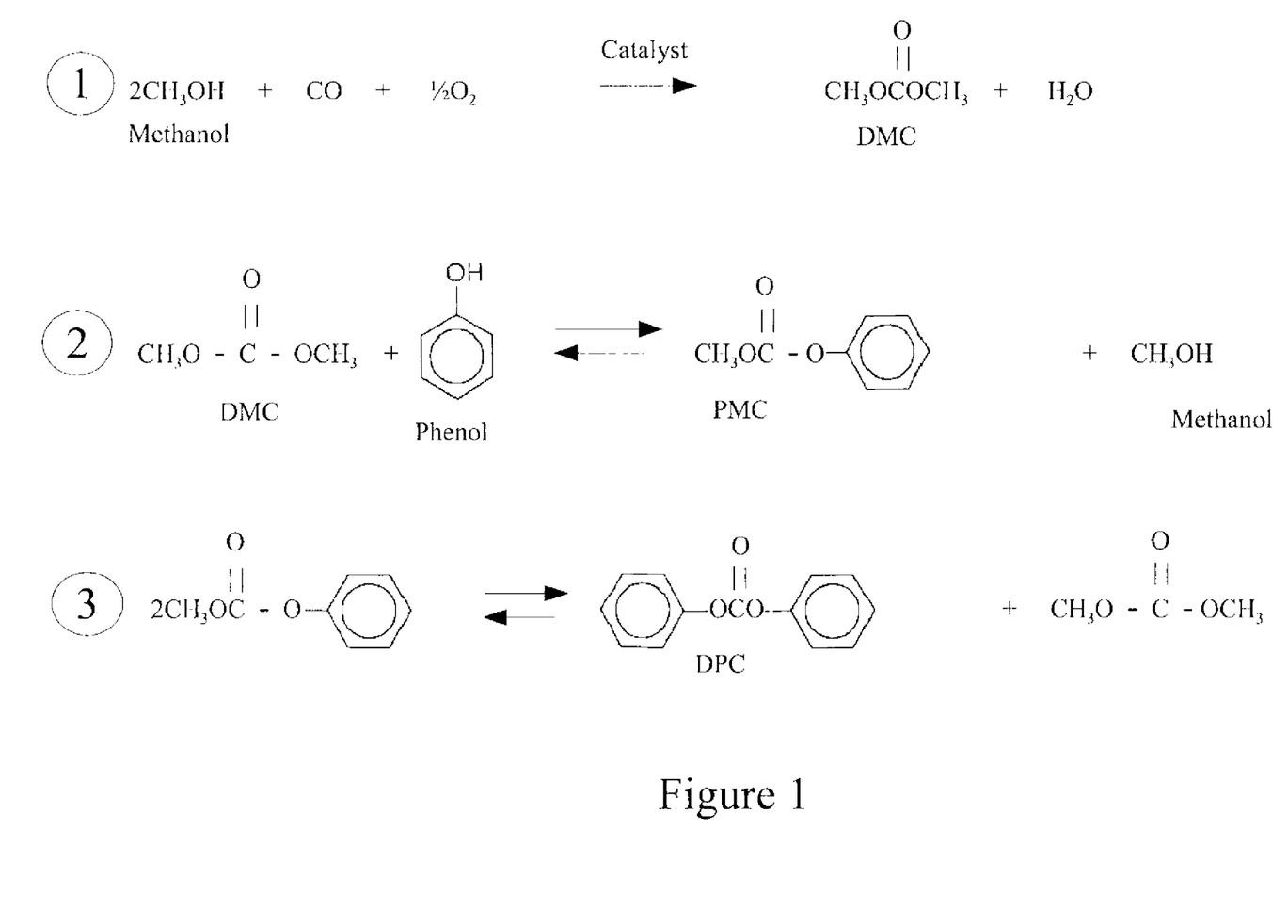
FIG. 1 is a reaction schematic diagram.

As shown schematically in FIG. 1, the non-phosgene process involves three reaction steps. First, a dialkyl carbonate (e.g. dimethyl carbonate) and water are formed by reacting an alkanol (e.g. methanol) with oxygen and carbon monoxide in the presence of a catalyst. In a second reaction step, the dialkyl carbonate reacts with an aromatic alcohol (e.g. phenol) to produce an arylalkyl carbonate (e.g. phenylmethyl carbonate) and an alkanol (e.g. methanol). Then, in the third reaction step, two molecules of an arylalkyl carbonate undergo a transesterification reaction to produce one molecule of diaryl carbonate (e.g. diphenyl carbonate) and one molecule of dialkyl carbonate. The present invention relates to the first step of this process.

As described above, the formation reaction to form dialkyl carbonate (step 1 of FIG. 1) reacts an alkanol with carbon monoxide and oxygen in the presence of a catalyst usually in a closed stirred tank reactor. It has been found that catalyst can build up on horizontal surfaces in the reactor, in transfer lines to and from the reactor, and in separation equipment used later in the production process. This catalyst buildup has two potential problems. The first problem is that the catalyst buildup can, over time, clog transfer lines to and from the reactor. Furthermore, the catalyst buildup in the transfer lines as well as the horizontal surfaces in the reactor can lead to solid catalyst "chunks" breaking loose and falling into the reactor or later separation equipment. If the "chunks" are big enough they may interfere with and potentially damage the reactors agitation propellers or cause vibration and damaging conditions within separation equipment.

To avoid these events a dialkyl carbonate production facility would have to be shut down to clean the reactors, transfer lines, and separation equipment to remove any catalyst buildup that had occurred. The time the dialkyl carbonate production facility was shut down would create shortages to downstream consumers or processes that require a consistent stream of dialkyl carbonate. It would be extremely beneficial to find a process where catalyst buildup as described herein could be avoided and where a safe and equipment friendly process can produce a consistent stream of dialkyl carbonate.

SUMMARY OF THE INVENTION

The present inventors have found a process where catalyst buildup in reactors, transfer lines, and separation equipment in a dialkyl carbonate production facility can be avoided. As such the present inventors have found a process where a consistent stream of dialkyl carbonate could be produced safely without damage to process equipment. In one embodiment the present invention provides a method of forming dialkyl carbonate comprising:

(1) introducing reactants to a reactor having a gaseous head space and a liquid body space, the reactants comprising alkanol, carbon monoxide, oxygen, and a catalyst, the reactor operating under conditions to form dialkyl carbonate and water, wherein alkanol and the catalyst are introduced to the liquid body space of the reactor in a liquid, and wherein oxygen and carbon monoxide are introduced to the liquid body space of the reactor in a gas, (2) introducing a separate stream comprising oxygen to the head space of the reactor such that the head space comprises an oxygen content of between 0.10 mole % and 1.00 mole %, (3) removing a product stream from the head space of the reactor, the product stream comprising dialkyl carbonate, water, oxygen, and residual reactants, (4) introducing the product stream to a cyclonic separation device to produce a liquid bottom stream and a gaseous top stream, (5) capturing and introducing the liquid bottom stream from the cyclonic separation device to the reactor, wherein the gaseous top stream contains product dialkyl carbonate.

In a second embodiment, the present invention provides a method of forming dialkyl carbonate comprising:

(1) introducing reactants to a reactor having a gaseous head space and a liquid body space, the reactants comprising alkanol, carbon monoxide, oxygen, and a catalyst, the reactor operating under conditions to form dialkyl carbonate and water, wherein the reactor comprises a baffle, wherein the baffle is arranged in a configuration selected from the group consisting of:

(A) the baffle is entirely disposed within the liquid body space of the reactor, and (B) the baffle comprises a portion that is disposed in the gaseous head space and a portion that is disposed in the liquid body space, wherein the baffle portion disposed in the gaseous head space comprises a less than 200 $cm^2$ of horizontal surfaces, (2) removing a product stream from the head space of the reactor, the product stream comprising dialkyl carbonate, water, and residual reactants, (3) introducing the product stream to a cyclonic separation device to produce a liquid bottom stream and a gaseous top stream, and (4) capturing and introducing the liquid bottom stream from the cyclonic separation device to the reactor, wherein the gaseous top stream contains product dialkyl carbonate.

In a third embodiment, the present invention provides a method of forming dialkyl carbonate comprising:

(1) introducing reactants to a reactor having a gaseous head space and a liquid body space, the reactants comprising alkanol, carbon monoxide, oxygen, and a catalyst, the reactor operating under conditions to form dialkyl carbonate and water, (2) removing a product stream from the head space of the reactor, the product stream comprising dialkyl carbonate, water, and residual reactants, (3) introducing the product stream and a liquid flushing stream to a cyclonic separation device to produce a liquid bottom stream and a gaseous top stream, wherein the liquid flushing stream comprises hydrochloric acid, (4) capturing the liquid bottom stream, wherein the liquid bottom stream comprises liquid condensed in the cyclonic separation device, liquid and solids entrained in the product stream, and liquid contained in the liquid flushing stream, and introducing the liquid bottom stream from the cyclonic separation device to the reactor, wherein the gaseous top stream contains product dialkyl carbonate.

DETAILED DESCRIPTION

The present inventors have found processes where catalyst buildup in reactors, transfer lines, and separation equipment in a dialkyl carbonate production facility can be reduced and even eliminated. The processes and embodiments described herein to accomplish the reduction in catalyst buildup can be used alone or in combination with one another. These processes when employed separately or in combination provide a consistent stream of dialkyl carbonate from a dialkyl carbonate formation reactor system.

In the specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

Suitable alkanols include primary, secondary, and tertiary $C_1$-$C_{12}$ alkanols, with primary $C_1$-$C_6$ alkanols being preferred. Highly preferred alkanols include methanol.

Suitable dialkyl carbonates are those that include a carbonate group disposed between two alkyl groups. The dialkyl carbonate formation reaction, such as that as depicted in FIG. 1, will create a dialkyl carbonate which is dependent upon the alkanol used as a reactant. For example, if methanol is used as a reactant, the dialkyl carbonate will comprise dimethyl carbonate, which is a preferred dialkyl carbonate.

Suitable diaryl carbonates include those that are used to effect a transesterification reaction between the free-hydroxy ends of dihydroxy compounds to form polycarbonate. Diaryl carbonates include a carbonate group disposed between two aryl groups. The diaryl carbonate formation reaction depicted in FIG. 1 will create a diaryl carbonate which is dependent upon the aromatic alcohol used as a reactant. If phenol is used as a reactant, the diaryl carbonate will comprise diphenyl carbonate, which is a preferred diaryl carbonate.

(1) Cyclonic Separation Device and a Liquid Flushing Stream

The present inventors have found that catalyst buildup in the separation equipment and transfer lines separation equipment and the reactor can be reduced and even eliminated if a liquid flushing stream is introduced to the cyclonic separation device. This flushing stream serves to prevent catalyst from adhering to the sides of the cyclonic separation device as well as the return pipe to reactor. Also, it is believed that the liquid flushing stream prevents catalyst that does become adhered to the cyclonic separation device and the return pipe from drying out and building up and clogging these pieces of equipment.

Figure 2:
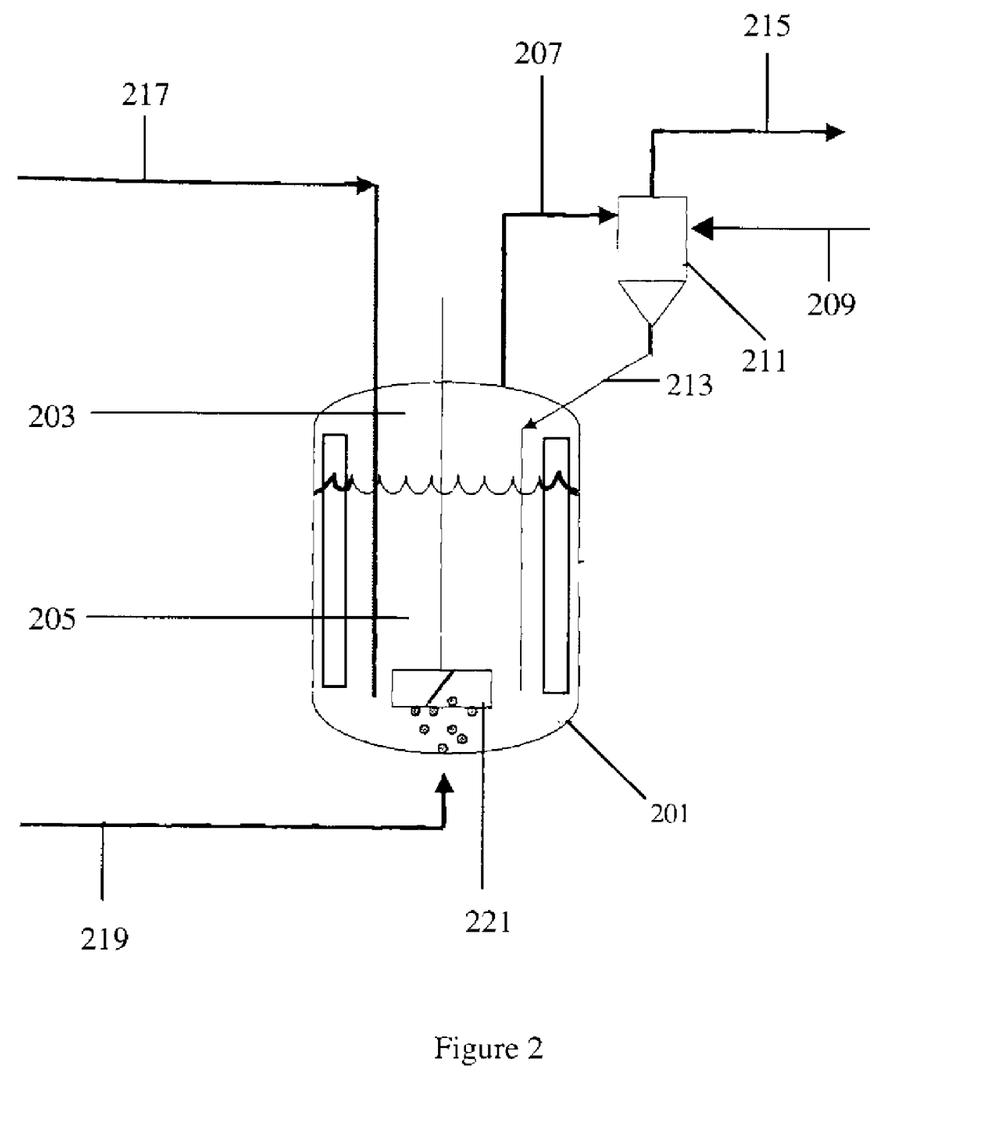
FIG. 2 is a schematic diagram showing dialkyl carbonate production equipment.

The present embodiment will be described herein with reference to FIG. 2. In this first embodiment, the present invention provides a method of forming dialkyl carbonate. A first step of this method includes introducing reactants to a reactor 201 having a gaseous head space 203 and a liquid body space 205. The reactor 201 is operating under conditions to form dialkyl carbonate and water according to the reaction scheme in FIG. 1. The reactants comprise alkanol, carbon monoxide, oxygen, and a catalyst. In a preferred embodiment alkanol and catalyst are introduced to the liquid body space 205 of the reactor 201 in a liquid stream 217 or streams. An alkanol reactant stream introduced to the reactor 201 may further comprise dialkyl carbonate that is difficult to separate in downstream product recovery steps because of the azeotropic nature of the product stream containing alkanol and dialkyl carbonate leaving the reactor. Oxygen and carbon monoxide are preferably introduced to the liquid body space 205 of the reactor 201 in gas stream 219. The reaction mixture in liquid body space 205 is preferably stirred by propeller 221.

The reactor 201 is operated under conditions sufficient to produce dialkyl carbonate and water. As described herein the reaction of alkanol with oxygen and carbon monoxide in the presence of a catalyst to produce dialkyl carbonate is well-known in the art and is described in U.S. Pat. Nos. 6,784,277 and 7,141,641, which are incorporated herein by reference. In these patents, it is described that the catalyzed reaction of the alkanol, oxygen, and carbon monoxide may be performed in a single reactor 201. The conditions for performing this reaction should be selected to maximize the yield of dialkyl carbonate while minimizing the degradation of dialkyl carbonate. Preferably, at a temperature of about 50° C. to about 250° C. and preferably at least about 100° C. for example up to about 150° C. The reactor 201 is preferably kept at a pressure of about 15 to about 35 bar gauge (bar) and preferably at least about 20 bar up to about 28 bar. The catalyst concentration should be sufficiently high to produce an acceptable yield, but should be kept below a concentration that would cause solid setting of the catalyst in the reactor 201.

Oxygen may be provided in any form, with gaseous forms being preferred. Suitable oxygen sources include, for example, air, and oxygen-containing gases having at least about 95 weight percent molecular oxygen, preferably at least about 99 weight percent molecular oxygen. Carbon monoxide is preferably supplied as a gas having at least about 90 weight percent, preferably at least about 95 weight percent, more preferably at least about 99 weight percent, carbon monoxide.

The reactants including the alkanol, oxygen, and carbon monoxide are preferably added in a molar ratio of (about 0.5 to about 0.7):(about 0.04 to about 0.06):(about 0.8 to about 1.2), respectively. A highly preferred molar ratio of alkanol:oxygen:carbon monoxide is (about 0.6):(about 0.05):(about 1).

Suitable catalyst include those comprising iron, copper, nickel, cobalt, zinc, ruthenium, rhodium, palladium, silver, cadmium, rhenium, osmium, iridium, platinum, gold, mercury, and the like, and combinations comprising at least one of the foregoing metals. Preferred catalysts may comprise copper. A highly preferred catalyst comprises copper and chloride ion in a molar ratio of about 0.5 to about 1.5. Within this range, a molar ratio of at least about 0.8 may be preferred. Also within this range, a molar ratio of up to about 1.2 may be preferred. Highly preferred catalysts include cuprous chloride (CuCl) and cupric chloride ($CuCl_2$), with cuprous chloride being more highly preferred. During operation of the process, a suitable chloride ion concentration may be maintained by the addition of hydrochloric acid (HCl).

The amount of catalyst used relative to the reactants will depend on the identity of the catalyst. For example, when the catalyst comprises CuCl, a highly preferred catalyst concentration is about 140 to about 180 grams per liter of reaction mixture. Sufficient HCl is preferably added to reactor 201 during the course of the reaction to maintain a molar ratio of Cu:Cl close to 1.0. The concentration of HCl is preferably continuously determined and controlled by the addition of HCl. A typical mass ratio for HCl feed to total liquid feed is about $6 \times 10^{-4}$ to about $8 \times 10^{-4}$.

A product stream 207 is removed from reactor 201 from the head space 203 of the reactor 201 in gaseous (gas/vapor) form. The product stream 207 comprises dialkyl carbonate, water, and residual reactants. The term "residual reactants" is herein understood to mean leftover reactants that were not reacted to form dialkyl carbonate. Residual reactants include alkanol, oxygen, carbon monoxide, and catalyst (e.g. CuCl and HCl). The term gaseous means that gas and vapor are present in the stream. The term "vapor" is meant to refer to organic fluid components of the mixture such as, for example, evaporated dialkyl carbonates, alkanols, and water vapor. That is, the term "vapor" refers to fluids having a boiling point of at least −50° C. at one atmosphere. In contrast, the term "gas" is meant to refer to the oxygen, carbon dioxide, carbon monoxide, and optionally nitrogen. That is, the term "gas" refers to fluids having a boiling point less than −50° C. at one atmosphere.

The gaseous product stream 207 and a liquid flushing stream 209 are introduced to a cyclonic separation device 211, preferably a cyclone 211. The cyclone 211 is operating under conditions sufficient to produce a liquid bottom stream 213 and a gaseous top stream 215. The material makeup of the liquid flushing stream 209 is preferably selected such that it comprises materials that are contained in the reactor 201 and not foreign to the reaction occurring in reactor 201. In one embodiment, the liquid flushing stream 209 comprises a material selected from the group consisting of alkanol, dialkyl carbonate, water, and combinations thereof. In a further preferred embodiment the liquid flushing stream may further comprises aqueous hydrochloric acid to provide a liquid flushing stream 209 comprising a material selected from the group consisting of alkanol, dialkyl carbonate, water, hydrochloric acid, and combinations thereof. In another preferred embodiment the liquid flushing stream 209 consists of aqueous hydrochloric acid. If hydrochloric acid is present in the liquid flushing stream it is preferable that it is present in a concentration greater than or equal to the concentration of hydrochloric acid in product stream 207. The liquid flushing stream may be introduced to the cyclone 211 individually or combined with product stream 207 prior to entering the cyclone 211. The temperature of the liquid flushing stream is preferably selected to be at or near to the temperature of the product stream 207 so as not to condense organic vapor present in the product stream 207.

The origin of the liquid flushing stream 209 is not particularly limited. In one embodiment, the liquid flushing stream 209 preferably is obtained from the liquid body space 205 of the reactor 201. The liquid flushing stream may also be obtained from a side draw from reactant stream 217 or optionally from individual reactant streams and introduced to the reactor 201 through cyclone 211.

The flow rate of the liquid flushing stream is selected such that catalyst buildup does not occur in the cyclone or in the bottom liquid stream 213 from the cyclone 211. Furthermore, the flow rate of the liquid flushing stream should be selected dependent upon the size of liquid bottom line 213. In a preferred embodiment, the flow rate of the liquid flushing stream 209 is selected such that liquid buildup in the cyclone does not occur. For example, where the liquid bottom stream 213 flows to the reactor in a pipe having a selected diameter the flow rate of the liquid flushing stream should be in the neighborhood of between 0.05 and 10 meters/second, more preferably between 0.05 and 5 meters per second, and most preferably between 0.05 and 2 meters/second to ensure adequate flushing of the cyclone and the transfer line.

The liquid bottom stream 213 is captured from cyclone 211 and introduced to the reactor 201. The liquid bottom stream 213 may be introduced in the gaseous head space 203 or in the liquid body space 205. In a preferred embodiment the liquid bottom stream 213 is introduced in the liquid body space 205, for example by means of a 'dip leg pipe' connected to the bottom of a cyclone 211 and directly into the liquid body space 205 of the reactor 201. The liquid bottom stream 213 comprises liquid condensed in the cyclone 211, liquid and solid entrained in the product stream 207, and liquid contained in the liquid flushing stream 209. The gaseous top stream 215 from the cyclonic separation device 211 contains product dialkyl carbonate and may be further refined. For Example as described in U.S. Pat. No. 7,141,641, which is incorporated herein by reference for all purposes, the gaseous top stream 215 may be introduced to a series of purification steps to produce a purified dialkyl carbonate product stream that is suitable for use in a diaryl carbonate production facility.

(2) Introduction of Oxygen to the Reactor Head Space

The present inventors have found that catalyst buildup can be reduced and even eliminated in the reaction and separation equipment if oxygen is introduced to the head space of the reactor. Furthermore, when catalyst buildup is observed using this embodiment, it has been found that the buildup is softer than it would be without adding oxygen to head space of the reactor. This is beneficial because if a chunk of catalyst were to break off it will be less likely to damage the equipment.

Figure 3:
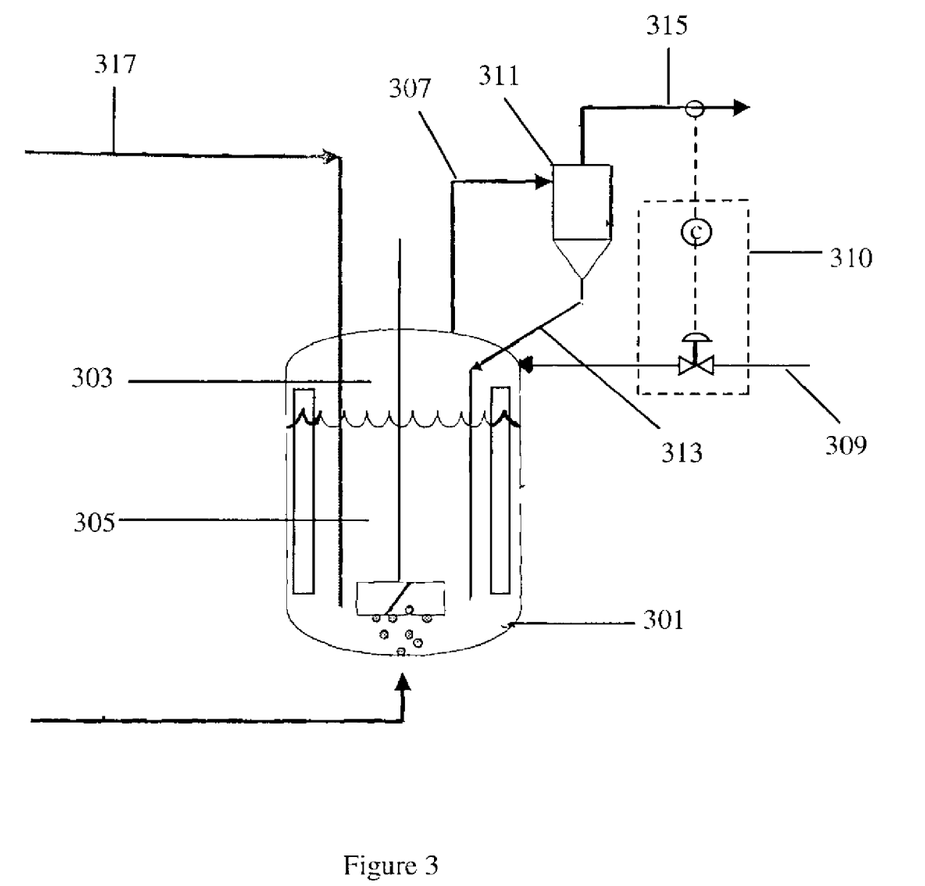
FIG. 3 is a schematic diagram showing dialkyl carbonate production equipment.

The present embodiment will be described herein with reference to FIG. 3. In this embodiment, the present invention provides another method of forming dialkyl carbonate. A first step of this method includes introducing reactants to a reactor 301. The reactor 301 has a gaseous head space 303 and a liquid body space 305. The reactants comprise alkanol, carbon monoxide, oxygen, and a catalyst. The reactor operates under conditions, as described above, to form dialkyl carbonate and water. Alkanol and the catalyst are introduced to the liquid body space 305 of the reactor 301 in a combined liquid 317 or separately in a plurality of individual reactant streams.

Oxygen and carbon monoxide are introduced to the liquid body space 305 of the reactor 301 preferably in gaseous form as described above.

The present inventors have found that catalyst buildup is reduced when oxygen is present in the head space 303 of the reactor 301. Therefore, in the present embodiment, a separate stream 309 comprising oxygen is introduced to the head space 303 of the reactor 301. The source of stream 309 is not particularly limited and preferably comprises a mixture of carbon monoxide and oxygen in a similar stoichiometric ratio added to the liquid space 305 of the reactor, for example 1:1. In a preferred embodiment the flow rate of steam 309 will be selected such that the head space 303 of the reactor 301 comprises an oxygen content of between 0.10 mole % and 1.00 mole %, and more preferably between 0.20 and 0.6 mole % (for example between 0.30 and 0.50 mole %). In another preferred embodiment the flow rate of stream 309 is controlled using a controller and valve assembly 310. In this later embodiment, the flow rate of stream 309 is controlled such that oxygen is also present in the ranges described above in the top gaseous stream 315 from the cyclonic separation device 311.

A gaseous product stream 307 is removed from the head space 303 of the reactor 301. The product stream 307 comprises dialkyl carbonate and water formed in the reactor, oxygen introduced via stream 309, and residual unreacted reactants. The product stream is introduced to a cyclonic separation device 311, preferably cyclone 311, to produce a liquid bottom stream 313 and a gaseous top stream 315. The liquid bottom stream 313 is captured and introduced to the reactor 301, as described above. The gaseous top stream 315 contains product dialkyl carbonate.

(3) Preferred Baffle Configurations

The present inventors have found that catalyst buildup can be reduced and even eliminated in the reaction equipment if a preferred baffle configuration is employed. It has been found that catalyst buildup can occur on horizontal surfaces within the reaction and separation equipment. Catalyst can adhere to these horizontal surfaces, dry, and eventually buildup. When left unchecked chunks from the buildup can break off and fall into the liquid space of the reactor and separation equipment thereby causing damage to equipment and potentially unsafe vibration in the equipment. Therefore, the inventors have determined that horizontal surfaces in the reactor, and in particular baffles and their supporting brackets having portions disposed in the gaseous head space of the reactor should be minimized. The term "horizontal surface" means a surface that is substantially horizontal and is herein understood to mean that the surface is flat and contains a slope with respect to the horizontal plane of less than 20°, for example 10° or less.

Figure 4A:
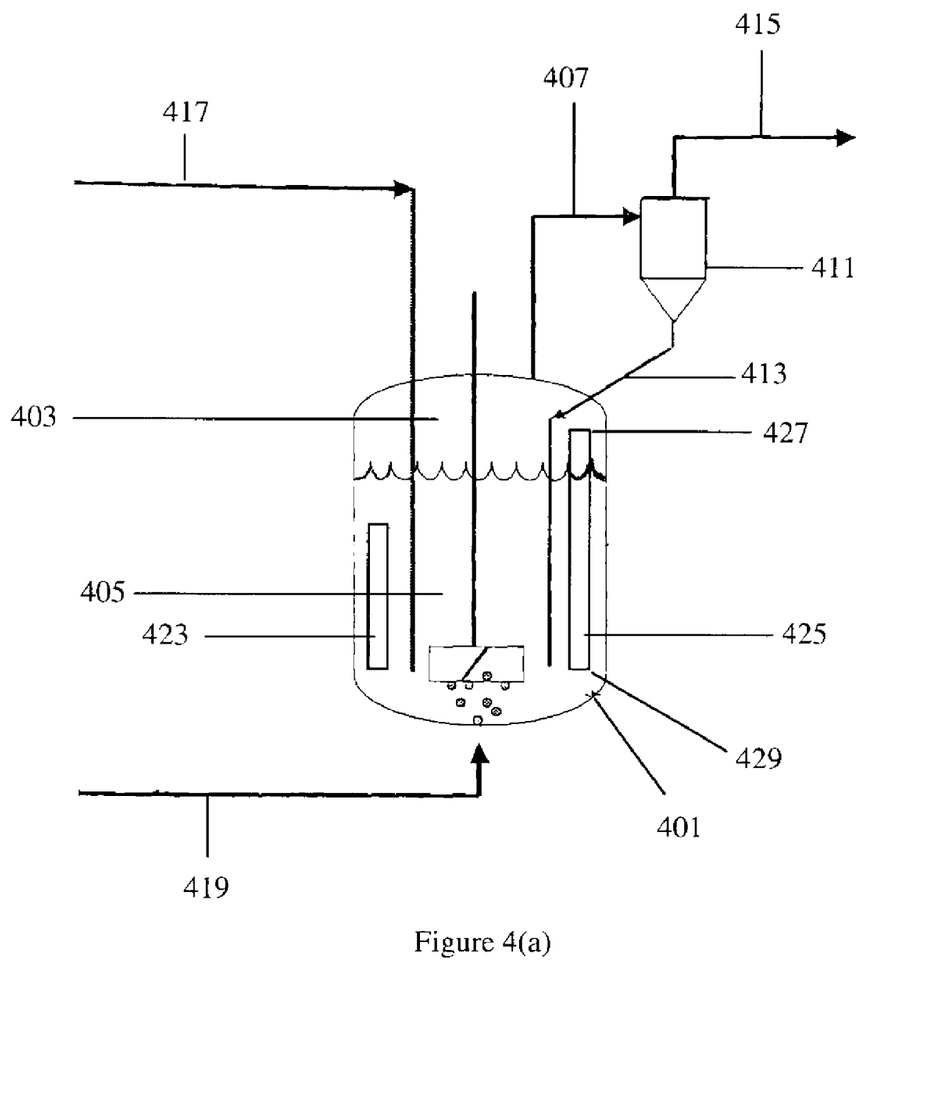
FIG. 4(a) is a schematic diagram showing dialkyl carbonate production equipment.

The present embodiment will be described herein with reference to FIGS. 4(*a*)-(*c*). In this embodiment, the present invention provides another method of forming dialkyl carbonate. A first step of this method includes introducing reactants to a reactor 401. The reactor 401 has a gaseous head space 403 and a liquid body space 405. The reactants comprise alkanol, carbon monoxide, oxygen, and catalyst. The reactor 401 operates under conditions, as described above, to form dialkyl carbonate and water. Alkanol and the catalyst are introduced to the liquid body space 405 of the reactor 401 in a combined liquid 417 or separately in a plurality of individual reactant streams. Oxygen and carbon monoxide are introduced, preferably in stream 419 or in separate streams, to the liquid body space 405 of the reactor 401 preferably in gaseous form as described above.

The reactor comprises a baffle (423 or 425) or a plurality of baffles (423 and 425). The term "baffle" is herein understood to include the vertical baffle portion as well as any attachment 451 or supporting bracket 451 that attaches the vertical baffle portion to the reactor 401. The baffle or baffles are arranged in a configuration selected from the group consisting of:

(A) the baffle 423 is entirely disposed within the liquid body space 405 of the reactor 401, and (B) the baffle 425 comprises a portion 427 that is disposed in the gaseous head space 403 and a portion 429 that is disposed in the liquid body space 405, wherein the baffle portion 427 of any one baffle, including any attachments as described above, disposed in the gaseous head space 403 has a horizontal surface area of less than 200 cm$^2$.

Figure 4B:
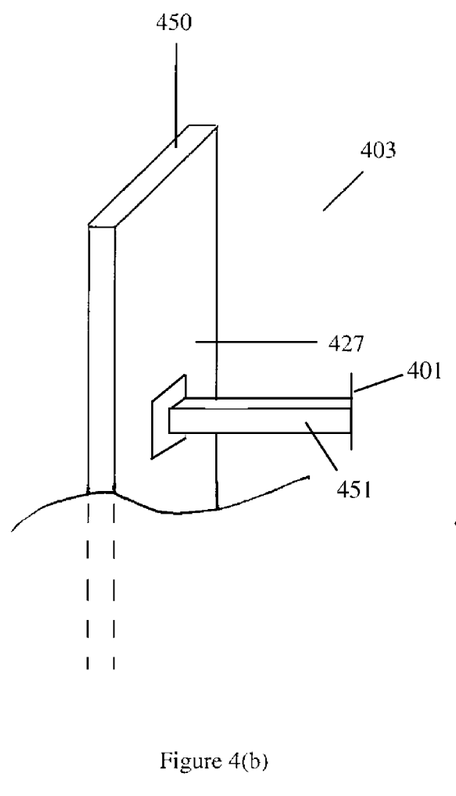
FIGS. 4(b) and 4(c) are schematic diagrams showing baffle configurations in dialkyl carbonate production equipment.
Figure 4C:
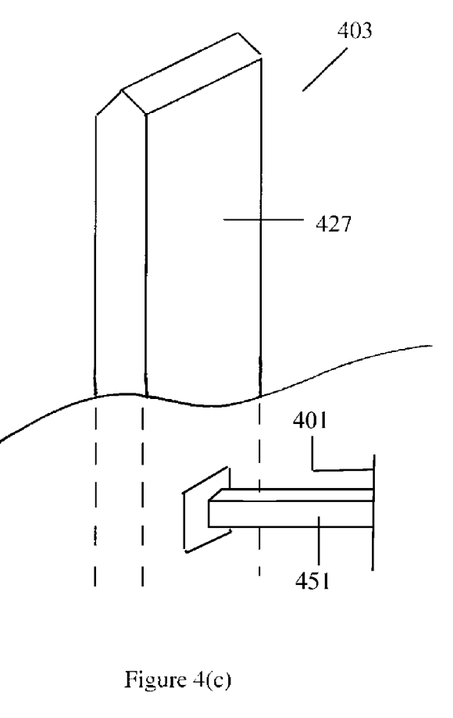

As shown in FIG. 4(*b*) if baffle configuration (B) is selected and employed the baffle portion 427, including any attachments as described above, disposed in the gaseous head space 403 will preferably have less than 100 cm$^2$ of horizontal surface area 450. As shown in FIG. 4(*c*) the baffle portion 427 disposed in the gaseous head space 403 will have no horizontal surfaces. The reduction of horizontal surfaces may be achieved by tapering the top of the baffle as depicted in FIG. 4(*c*).

A product stream 407 is removed from the head space 403 of the reactor 401. The product stream 407 comprises dialkyl carbonate, water, and residual reactants and is introduced to a cyclonic separation device 411 to produce a liquid bottom stream 413 and a gaseous top stream 415. The liquid bottom stream 413 is captured from the cyclonic separation device 411 and introduced to the reactor 401. The gaseous top stream 415 contains product dialkyl carbonate.

COMBINATIONS OF METHOD EMBODIMENTS

Figure 5:
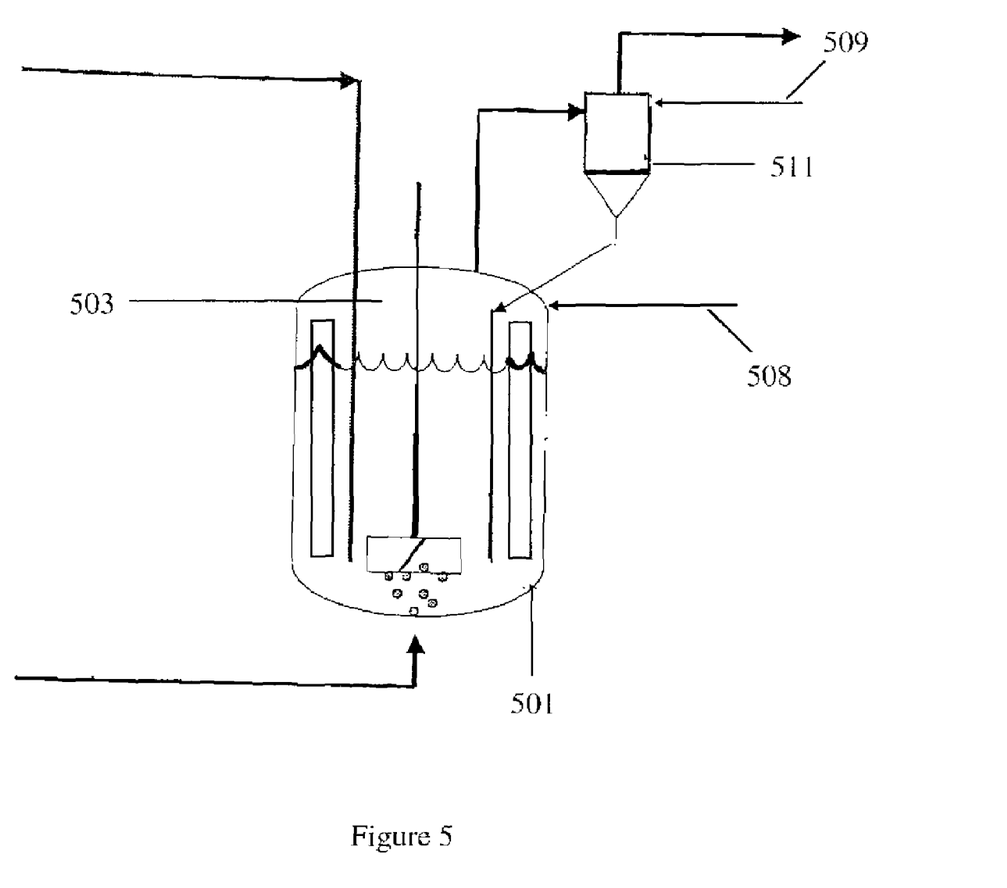
FIG. 5 is a schematic diagram showing dialkyl carbonate production equipment.
Figure 6:
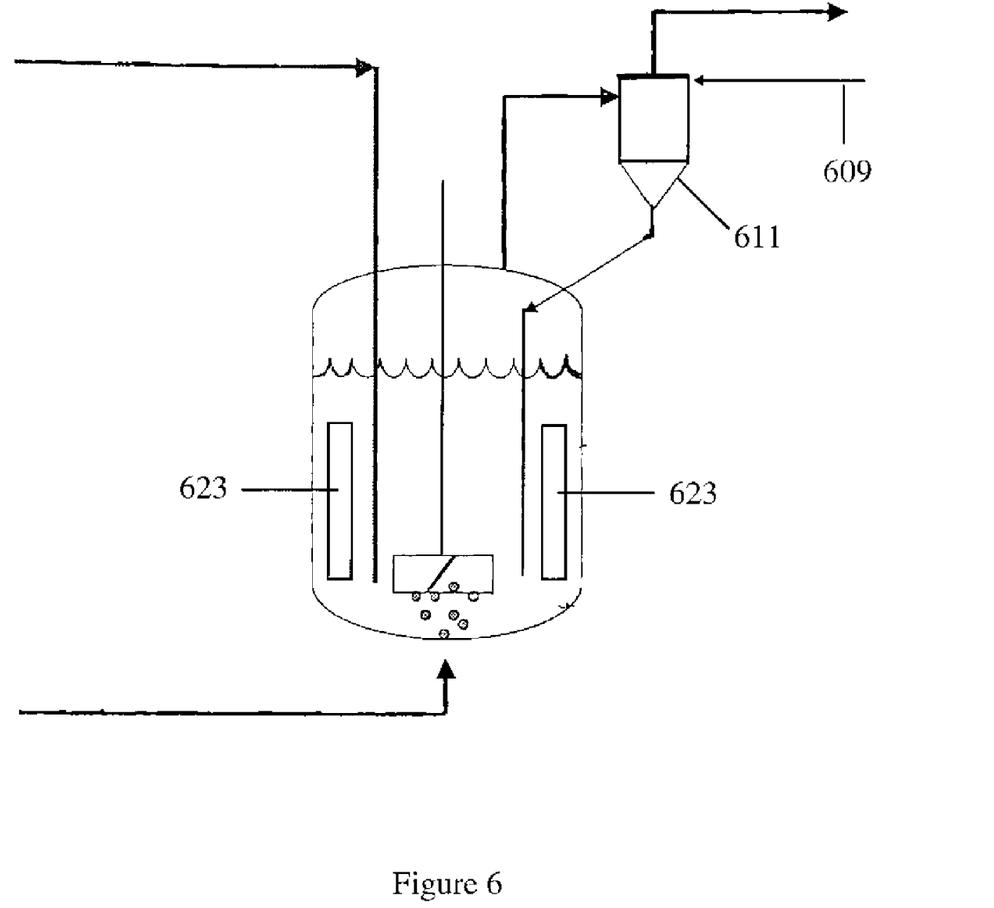
FIG. 6 is a schematic diagram showing dialkyl carbonate production equipment.
Figure 7:
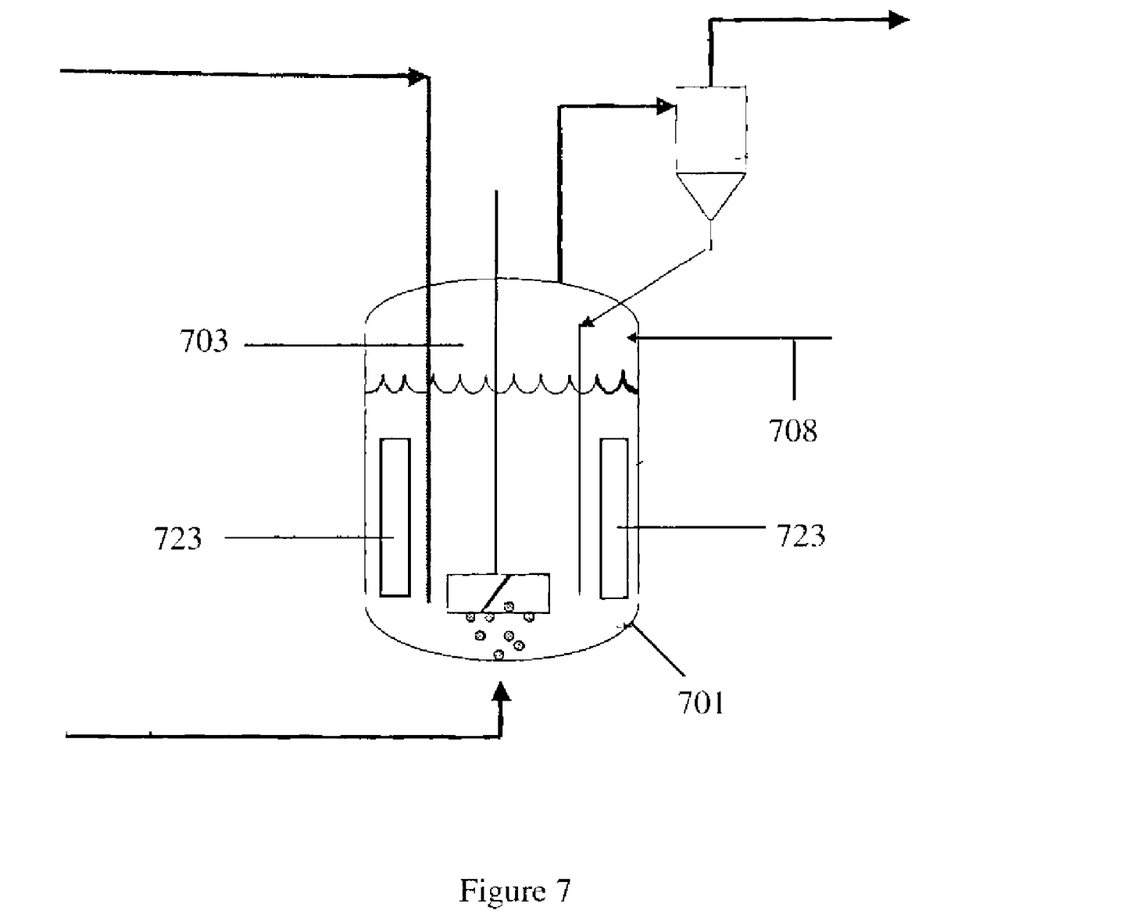
FIG. 7 is a schematic diagram showing dialkyl carbonate production equipment.
Figure 8:
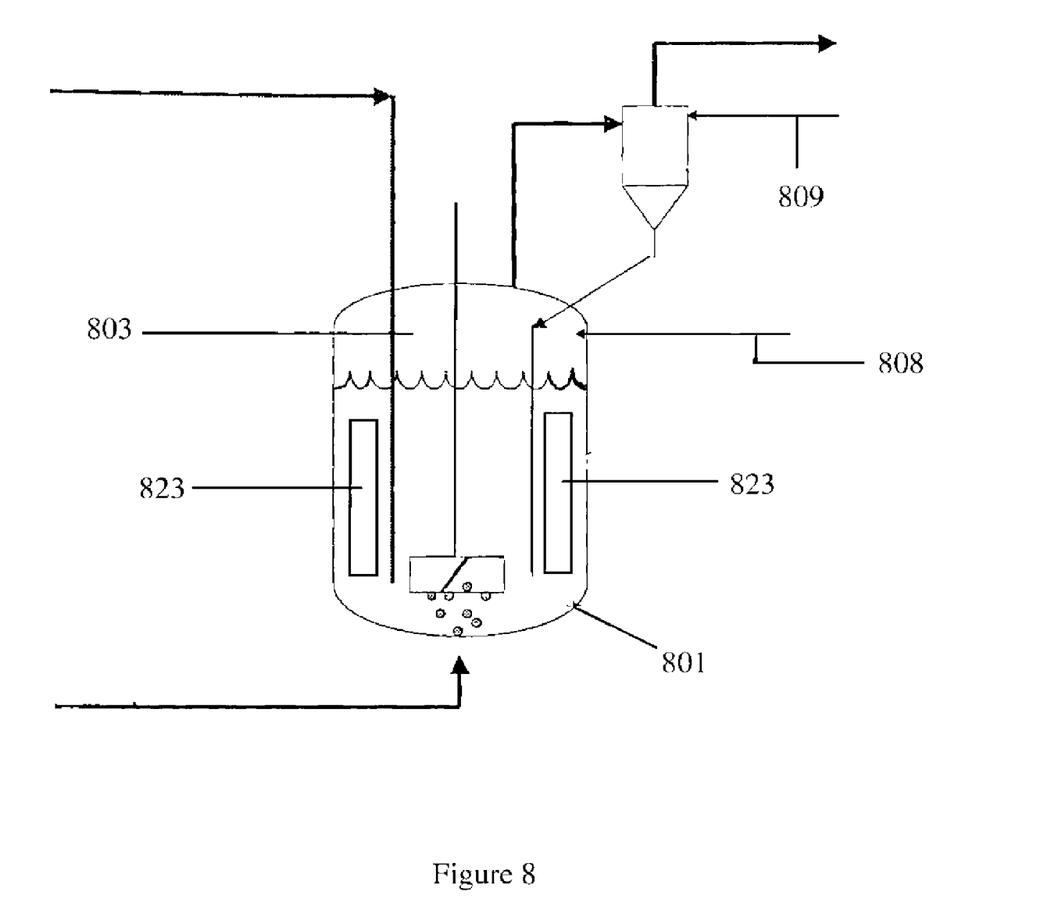
FIG. 8 is a schematic diagram showing dialkyl carbonate production equipment.

As described herein the present invention provides methods of producing dialkyl carbonate wherein catalyst buildup in the reaction equipment, separation equipment, and transfer lines can be reduced and even eliminated. The present invention provides at least three novel methods for accomplishing this objective. The methods may be used alone or they may be used in any combination. For example as described in FIG. 5, the first and second embodiments that include (1) introducing a liquid flushing stream 509 to the cyclonic separation device 511 and (2) introducing a separate stream 508 comprising oxygen to the head space 503 of the reactor 501 are employed. As depicted in FIG. 6, the first and third embodiments that include (1) introducing a liquid flushing stream 609 to the cyclonic separation device 611 and (3) employing a preferred baffle 623 configuration as described above are employed. As described in FIG. 7, and the second and third method embodiments that include (2) introducing a separate stream 708 comprising oxygen to the head space 703 of the reactor 701 and (3) employing a preferred baffle 723 configuration as described above are employed. In a most preferred, embodiment depicted in FIG. 8 all three method embodiments are employed that include (1) introducing a liquid flushing stream 809 to the cyclonic separation device 811, (2) introducing a separate stream 808 comprising oxygen to the head space 803 of the reactor 801, and (3) employing a preferred baffle 823 configuration as described above. Note that the baffle configuration employed in FIGS. 6 through 8 include a preferred configuration wherein the baffles are entirely disposed with the liquid body space of the reactors.

EXAMPLES

Having described the invention in detail, the following examples are provided. The examples should not be considered as limiting the scope of the invention, but merely as illustrative and representative thereof.

Illustration 1 (Oxygenation and Catalyst Buildup Reduction)

A reaction mixture was prepared and reacted according to the following conditions. The reaction mixture comprised methanol (MeOH) dimethyl carbonate (DMC) is a ratio of 70:30 wt %. The reaction mixture also contained 16 grams of CuCl. This mixture was introduced to a closed glass reactor with a volume of 100 ml. The reactor was maintained at 350 psi and a temperature of 132° C. The reaction mixture was stirred with an agitator rotating at a speed of 1,000 RPM. An oxidation gas feed comprising $N_2$:$O_2$ at a 95:5 ratio was introduced to the reactor at a flow rate of 1200 Nml/min for two hours. A reaction gas feed comprising carbon monoxide and oxygen (CO:$O_2$) at a 95:5 ratio was also introduced to the glass reactor at a flow rate of 660 Nml/min for 3 hours. The reaction mixture was then reduced with CO for 8 hrs with a CO gas flow at a rate of 660 NMl/min 1,000 RPM. The reaction mixture was then kept under CO at a pressure 350 psi without flow and without stirring @132° C. for 7 days.

At the end of 7 days the reactor was opened and visually inspected for catalyst lump formation. Catalyst lumps were found in and above the reaction mixture liquid level. The reactor was closed and stirred at 1,000 RPM for 2 hours at 132° C. and 350 psi CO pressure. At the end of this 2 hour period the agitator was stopped and the reactor was opened and visually inspected for catalyst lump formation. Catalyst lumps were again observed in the reaction mixture and above the liquid level in the reactor. The reactor was closed and a stirred at 1,000 RPM for 2 hours at 132° C. During this time a stream comprising $N_2$ and $O_2$ at a ratio of 95:5 was also introduced to the reactor. At the end of this 2 hour time period the agitator was stopped and the reactor was opened and no lumps were found in the reaction mixture or above the liquid level in the reactor.

It can be concluded that the catalyst buildup in the form of lumps is observed when the head space of a reactor is devoid of oxygen. When oxygen is introduced to the head space of the reactor catalyst buildup can be reduced and even eliminated.

The invention claimed is:

1. A method of forming dialkyl carbonate comprising:
   (1) introducing reactants to a reactor having a gaseous head space and a liquid body space, the reactants comprising alkanol, carbon monoxide, oxygen, and a catalyst, the reactor operating under conditions to form dialkyl carbonate and water,
      wherein alkanol and the catalyst are introduced to the liquid body space of the reactor in a liquid, and
      wherein oxygen and carbon monoxide are introduced to the liquid body space of the reactor in a gas,
   (2) introducing a separate stream comprising oxygen to the head space of the reactor such that the head space comprises an oxygen content of between 0.10 mole % and 1.00 mole %,
   (3) removing a product stream from the head space of the reactor, the product stream comprising dialkyl carbonate, water, oxygen, and residual reactants,
   (4) introducing the product stream to a cyclonic separation device to produce a liquid bottom stream and a gaseous top stream,
   (5) capturing and introducing the liquid bottom stream from the cyclonic separation device to the reactor,
      wherein the gaseous top stream contains product dialkyl carbonate.

2. The method of claim 1, wherein the head space comprises an oxygen content of between 0.20 mole % and 0.60 mole %.

3. The method of claim 1, wherein a liquid flushing stream is also introduced to the cyclonic separation device, wherein the liquid flushing stream comprises a material selected from the group consisting of alkanol, dialkyl carbonate, water, and combinations thereof, and wherein the liquid bottom stream comprises liquid condensed in the cyclonic separation device, liquid and solids entrained in the product stream, and liquid contained in the liquid flushing stream.

4. The method of claim 3, wherein the liquid flushing stream further comprises hydrochloric acid.

5. The method of claim 3, wherein the reactor comprises a baffle, wherein the baffle is arranged in a configuration selected from the group consisting of:
   (A) the baffle is entirely disposed within the liquid body space of the reactor, and
   (B) the baffle comprises a portion that is disposed in the gaseous head space and a portion that is disposed in the liquid body space, wherein the baffle portion of any one baffle disposed in the gaseous head space has a horizontal surface area of less than 200 $cm^2$.

6. The method of claim 5, wherein the baffle is arranged in configuration (B), wherein the baffle portion of any one baffle disposed in the gaseous head space has a horizontal surface area of less than 100 $cm^2$.

7. The method of claim 6, wherein the baffle comprises no horizontal surfaces.

8. The method of claim 1, wherein the reactor comprises a baffle, wherein the baffle is arranged in a configuration selected from the group consisting of:
   (A) the baffle is entirely disposed within the liquid body space of the reactor, and
   (B) the baffle comprises a portion that is disposed in the gaseous head space and a portion that is disposed in the liquid body space, wherein the baffle portion of any one baffle disposed in the gaseous head space has a horizontal surface area of less than 200 $cm^2$.

9. The method of claim 8, wherein the baffle is arranged in configuration (B), wherein the baffle portion of any one baffle disposed in the gaseous head space has a horizontal surface area of less than 100 $cm^2$.

10. The method of claim 1, wherein the catalyst comprises a mixture of copper chloride and hydrochloric acid.

11. The method of claim 10, wherein the baffle comprises no horizontal surfaces.

12. The method of claim 1, wherein the alkanol comprises methanol and the dialkyl carbonate comprises dimethyl carbonate.

13. A method of forming dialkyl carbonate comprising:
   (1) introducing reactants to a reactor having a gaseous head space and a liquid body space, the reactants comprising alkanol, carbon monoxide, oxygen, and a catalyst, the reactor operating under conditions to form dialkyl carbonate and water,
      wherein the reactor comprises a baffle, wherein the baffle is arranged in a configuration selected from the group consisting of:
      (A) the baffle is entirely disposed within the liquid body space of the reactor, and
      (B) the baffle comprises a portion that is disposed in the gaseous head space and a portion that is disposed in the liquid body space, wherein the baffle portion of any one baffle disposed in the gaseous head space has a horizontal surface area of less than 200 $cm^2$, (2) removing a product stream from the head space of the reactor, the product stream comprising dialkyl carbonate, water, and residual reactants, (3) introducing the product stream to a cyclonic separation device to produce a liquid bottom stream and a gaseous top stream, and (4) capturing and introducing the liquid bottom stream from the cyclonic separation device to the reactor, wherein the gaseous top stream contains product dialkyl carbonate.

14. The method of claim 13, wherein the baffle is arranged in configuration (B), wherein the baffle portion of any one baffle disposed in the gaseous head space has a horizontal surface area of less than 100 cm$^2$.

15. The method of claim 14, wherein the baffle comprises no horizontal surfaces.

16. The method of claim 13, wherein a liquid flushing stream is also introduced to the cyclonic separation device, wherein the liquid flushing stream comprises a material selected from the group consisting of alkanol, dialkyl carbonate, water, and combinations thereof, and wherein the liquid bottom stream comprises liquid condensed in the cyclonic separation device, liquid and solids entrained in the product stream, and liquid contained in the liquid flushing stream.

17. The method of claim 16, wherein the liquid flushing stream further comprises hydrochloric acid.

18. The method of claim 13, wherein the catalyst comprises a mixture of copper chloride and hydrochloric acid.

19. The method of claim 13, wherein the alkanol comprises methanol and the dialkyl carbonate comprises dimethyl carbonate.

20. A method of forming dialkyl carbonate comprising:
(1) introducing reactants to a reactor having a gaseous head space and a liquid body space, the reactants comprising alkanol, carbon monoxide, oxygen, and a catalyst, the reactor operating under conditions to form dialkyl carbonate and water, (2) removing a product stream from the head space of the reactor, the product stream comprising dialkyl carbonate, water, and residual reactants, (3) introducing the product stream and a liquid flushing stream to a cyclonic separation device to produce a liquid bottom stream and a gaseous top stream, wherein the liquid flushing stream comprises hydrochloric acid, (4) capturing the liquid bottom stream, wherein the liquid bottom stream comprises liquid condensed in the cyclonic separation device, liquid and solids entrained in the product stream, and liquid contained in the liquid flushing stream, and introducing the liquid bottom stream from the cyclonic separation device to the reactor, wherein the gaseous top stream contains product dialkyl carbonate.

21. The method of claim 20, wherein the concentration of hydrochloric acid in the liquid flushing stream is greater than or equal to the concentration of hydrochloric acid in the product stream.

22. The method of claim 20, wherein the liquid flushing stream further comprises a material selected from the group consisting of alkanol, dialkyl carbonate, water, and combinations thereof.

* * * * *

UNITED STATES PATENT AND TRADEMARK OFFICE
CERTIFICATE OF CORRECTION

PATENT NO. : 7,799,940 B2
APPLICATION NO. : 12/032149
DATED : September 21, 2010
INVENTOR(S) : Fernandez et al.

It is certified that error appears in the above-identified patent and that said Letters Patent is hereby corrected as shown below:

Column 10, Claim 10, Lines 46 through 47 should read: -- The method of claim 9, wherein the baffle comprises no horizontal surfaces. --

Column 10, Claim 11, Lines 48 through 49 should read: -- The method of claim 1, wherein the catalyst comprises a mixture of copper chloride and hydrochloric acid. --

Signed and Sealed this

Twenty-third Day of November, 2010

David J. Kappos
*Director of the United States Patent and Trademark Office*